United States Patent
Large

Patent Number: 5,712,721
Date of Patent: Jan. 27, 1998

[54] SWITCHABLE LENS

[75] Inventor: Timothy Andrew Large, Cambridge, United Kingdom

[73] Assignee: Technology Partnership, PLC, Royston, United Kingdom

[21] Appl. No.: 530,224

[22] PCT Filed: Apr. 7, 1994

[86] PCT No.: PCT/GB94/00742

§ 371 Date: Oct. 3, 1995

§ 102(e) Date: Oct. 3, 1995

[87] PCT Pub. No.: WO94/23334

PCT Pub. Date: Oct. 13, 1994

[30] Foreign Application Priority Data

Apr. 7, 1993 [GB] United Kingdom ............... 9307241
Jul. 6, 1993 [GB] United Kingdom ............... 9313952

[51] Int. Cl.$^6$ .................. G02F 1/03; G02C 1/00
[52] U.S. Cl. .............. 359/245; 359/256; 359/483; 359/494; 359/558; 351/158; 351/41; 351/44; 351/168
[58] Field of Search .................. 359/245, 246, 359/251, 253, 254, 256, 62, 63, 64, 55, 56, 57, 58, 494, 495, 483, 558; 351/41, 44, 158, 161, 168, 159

[56] References Cited

U.S. PATENT DOCUMENTS

| | | |
|---|---|---|
| 4,190,330 | 2/1980 | Berreman . |
| 4,564,267 | 1/1986 | Nishimoto .................. 359/483 |
| 4,572,616 | 2/1986 | Kowel . |
| 4,601,545 | 7/1986 | Kern .................. 349/200 |
| 4,795,248 | 1/1989 | Okada .................. 351/158 |
| 4,968,127 | 11/1990 | Russell et al. .................. 351/44 |
| 4,981,342 | 1/1991 | Fiala . |
| 5,015,086 | 5/1991 | Okaue et al. .................. 351/44 |
| 5,066,301 | 11/1991 | Wiley . |
| 5,073,021 | 12/1991 | Marron .................. 351/168 |
| 5,091,801 | 2/1992 | Ebstein . |
| 5,108,169 | 4/1992 | Mandell .................. 351/161 |
| 5,142,411 | 8/1992 | Fiala .................. 359/494 |
| 5,171,266 | 12/1992 | Wiley et al. . |
| 5,182,585 | 1/1993 | Stoner .................. 351/41 |
| 5,184,156 | 2/1993 | Black et al. .................. 351/158 |
| 5,229,885 | 7/1993 | Quaglia .................. 351/41 |
| 5,382,986 | 1/1995 | Black et al. .................. 351/158 |

FOREIGN PATENT DOCUMENTS 2169417 7/1986 United Kingdom .
2 170 613 8/1986 United Kingdom .

OTHER PUBLICATIONS

Kern, Seymour P., SPIE vol. 601, Ophthalmic Optics, 3–4 Dec. 1985, pp. 155–158.

*Primary Examiner*—Loha Ben
*Attorney, Agent, or Firm*—Watson Cole Stevens Davis, P.L.L.C

[57] ABSTRACT

A lens assembly (1) comprises a lens (2;10,11;20) the focal length of which may be changed by application of an electric or magnetic field. A switching means (4,15) provides a drive impulse to change the focal length of the lens (2;10,11;20). An integral power source (4,15) provides power for the switching means. A lens which can be switched between near and distance vision by the user is thereby provided.

24 Claims, 2 Drawing Sheets

SWITCHABLE LENS

BACKGROUND OF THE INVENTION

The present invention relates to a lens whose properties are variable.

The present invention has particular applicability in the area of bifocal lenses, and especially those used in ophthalmic applications, particularly contact lenses or intra-ocular lenses. Traditionally, contact and intra-ocular lenses have used a number of different techniques to allow users to see both near and distant objects. These techniques can be summarized as:

(i) Monovision—the user has lenses providing different focal lengths in each eye, one for near and one for distance vision.

(ii) Simultaneous vision—the eye of the user has both near and distant images focused on the retina simultaneously and the brain learns to distinguish the images and ignore the unwanted one; this may be achieved by the use of area division of the lens, polarization division, chromatic division, or bifocal diffractive lenses.

(iii) Translating bifocals—a prism ballast is incorporated to orientate the lens correctly in the eye. The lens moves up and down across the cornea depending on whether the eye looks up or down. When looking down, the user sees through a different optical power.

All of these techniques have particular disadvantages. The first two share the common disadvantage that the user is continuously confronted with two images. In many situations, this compromises the quality of vision. A particular example is that of driving at night, when the user sees both focused and blurred oncoming headlamps simultaneously which leads to an inability to see the road ahead clearly. Translating bifocals are based on the assumption that, when looking straight ahead, the user needs only distance vision and that, when looking down, the user needs only near vision. This is not always the case and is disadvantageous in many circumstances.

This invention aims to overcome these problems by providing a lens which can be switched between near and distance vision by the user. In the case of contact or intra-ocular lenses, the lens can be switched by the wearer; the user is therefore given the flexibility of a bifocal lens with the visual acuity of a monofocal lens.

The invention also has application in broader areas of optics. For example, it can provide a lens of variable focal length for use in compact disc players or optical memory disc drives.

SUMMARY OF THE INVENTION

According to the present invention, there is provided a lens assembly comprising:

- a lens having a property which may be switched by application of an electric or magnetic field, said property being at least one of the focal length, absorption, colour, and effective aperture;
- switching means to provide a drive impulse to switch the property of the lens; and,
- an integral power source to provide power for the switching means.

The power source may be a conventional miniature battery or a photocell, for example. In this latter case, the unit has no power source other than the light incident upon it. In its primary intended application as an ophthalmic lens, the power source may be a battery operable using the tear fluid for its activation.

In one preferred embodiment where the lens is used as an ophthalmic lens, the user can control the lens assembly by a deliberate (voluntary) eye action that is distinct from usual normal eye actions. An example of this is an extended blink. A normal involuntary blink lasts around 1/10 sec. A deliberate, longer blink (conveniently not so long as to look unnatural) could provide a trigger for the lens to change focal length. For implementations employing a photocell as power source, in very dark conditions, when the device is powered only to a very low level by the incident illumination, it can for example conveniently revert to a focal length which will provide distance vision.

It should be noted that the word "switch" is used in the following text primarily to refer to a change from one of two binary imaging states to the other. However, it should be read also to include an analogue change intermediate between those binary states. Such analogue switching could be useful in some applications (e.g. technical optics) where variable focal length, colour or aperture are desirable. For example, a variable focal length lens would have application in focus servo systems used in compact disc players.

The present invention is described in detail below only with reference to ophthalmic applications, although other applications should be understood.

BRIEF DESCRIPTION OF THE DRAWINGS

Examples of the present invention will now be described with reference to the accompanying drawings, in which.

DESCRIPTION OF THE INVENTION

Figure 1:
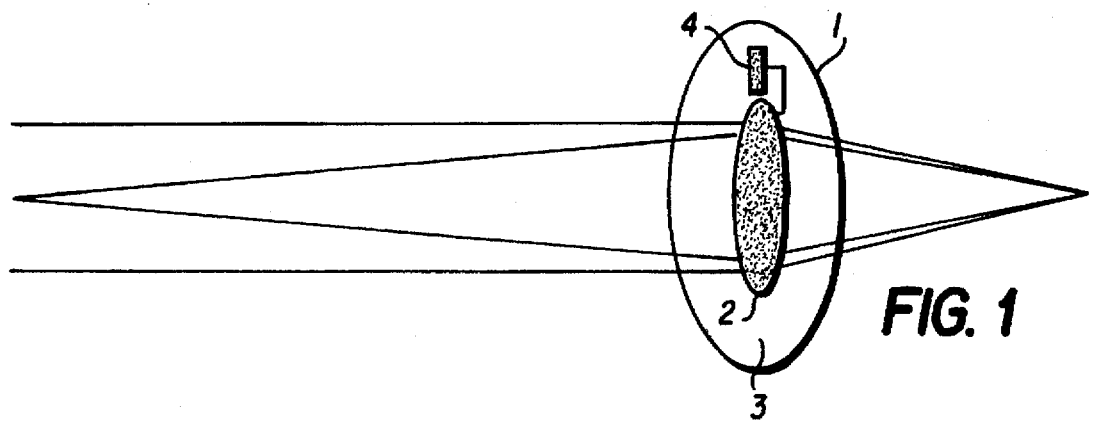
FIG. 1 is a schematic elevation of a lens assembly showing the general principles of the present invention.

In FIG. 1, there is shown a lens assembly 1 comprising an inner switchable lens 2 surrounded by a protective outer coating or lens 3 which encapsulates the switchable lens 2. A power source 4 is connected via circuitry 5 to the switchable lens 2 and allows the focal length, absorption, colour or effective aperture of the switchable lens 2 to be switched.

Figure 2:
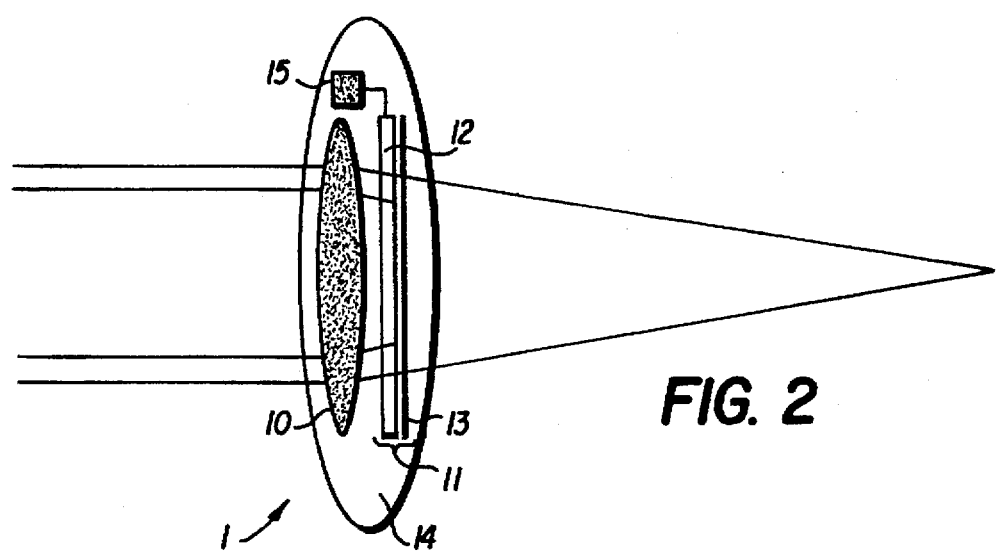
FIG. 2 is an elevation of a first example of a lens assembly according to the present invention; and, FIG. 3 is an elevation of a second example of a lens assembly according to the present invention.

A particular example of the present invention is illustrated in FIG. 2, this first example being particularly suited to intra-ocular lenses where the lens has a relatively large centre thickness. A birefringent lens 10 made from a fixed birefringent material (which may be of conventional refractive, Fresnel or diffractive form) is placed optically in series with a liquid crystal cell 11, consisting of a liquid crystal layer 12 and a polarizer layer 13. The birefringent lens 10 and the liquid crystal cell 11 are encased in a protective outer layer 14. A photocell and electronics circuitry 15 are provided within the protective outer layer 14 and are electrically connected to the liquid crystal layer 12.

The birefringent lens 10 produces a different focal length for each polarization of light incident upon it, as is well understood. The liquid crystal cell 11 may have the property that it may select one of the polarization states of light incident on it according to the electric field applied to the liquid crystal cell 11 by the photocell and circuitry 15. Consequently, the liquid crystal cell 11 may be used effectively to select either of the focal lengths of the birefringent lens 10. In the example shown in FIG. 2, the unwanted polarization state is absorbed by the polarizer layer 13. The polarizer layer 13 may be a layer separate from the liquid crystal layer 12.

Alternatively, the liquid crystal layer 12 may, by addition of a dichroic dye, in one state itself preferentially absorb one polarization, obviating the requirement for the distinct polarizer layer 13. In this case, when the liquid crystal in the liquid crystal layer 12 is undriven, one polarization of light is absorbed and the assembly 1 behaves as a monofocal lens (with focus selectable, as described in more detail below, to be one of the foci produced by the birefringent lens); when the liquid crystal in the liquid crystal layer 12 is driven, neither polarization of light is absorbed and the assembly 1 has two foci, so it behaves as a simultaneous vision device in that state.

In another alternative implementation, the liquid crystal layer 12 may be a cholesteric liquid crystal doped with a dichroic dye, such that in the undriven state the cell is dark or coloured (depending upon the absorption characteristics of the dye) and, in the driven state, the cell may be transparent. In this way, a lens of variable absorption or colour may be constructed. If the cell is further divided into locally driven regions, the lens may be made with an effectively variable aperture. An example of this geometry is to provide switchable absorption in an outer annulus of the lens. This can provide a lens whose focal length is fixed but whose optical resolution and depth of focus can be controlled.

In order to test the viability of the first example described with reference to FIG. 2, an assembly (not shown) has been constructed consisting of a liquid crystal lens as the birefringent lens 10, a switchable liquid crystal layer 12, a polarizer layer 13, photodiodes and an external switch. The liquid crystal lens 10 was constructed as a cell with one flat side and one spherically curved side, with a maximum height of 80 microns and a diameter of 8 mm. The lens cell walls were made of the ophthalmic plastics CR39, and filled with the high birefringence nematic liquid crystal Merck E44. The lens demonstrated two foci with optical powers of approximately 0 and +3 Dioptres. An unpatterned commercial twisted nematic liquid crystal cell with 25 mm by 25 mm active area and one polarizer in place was then placed optically in series with the lens. This cell demonstrated a switching voltage of 5V. Twelve photodiodes were placed electrically in series to provide a DC supply to the cell via a manual switch. The finished device, powered by ambient light, has been demonstrated and a switchable adjustment between optical powers of approximately 0 and +3D have been measured, even in dim room lighting.

Figure 3:
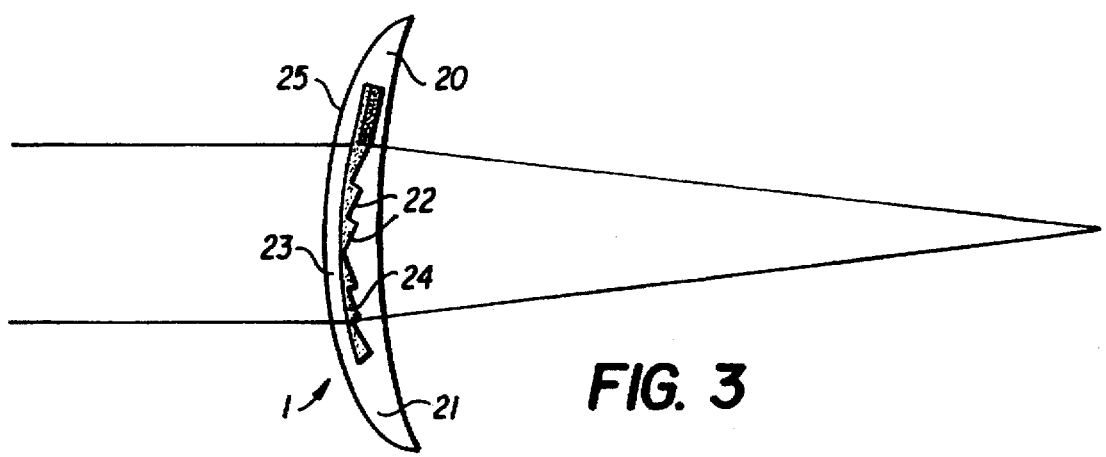
Figure 4:
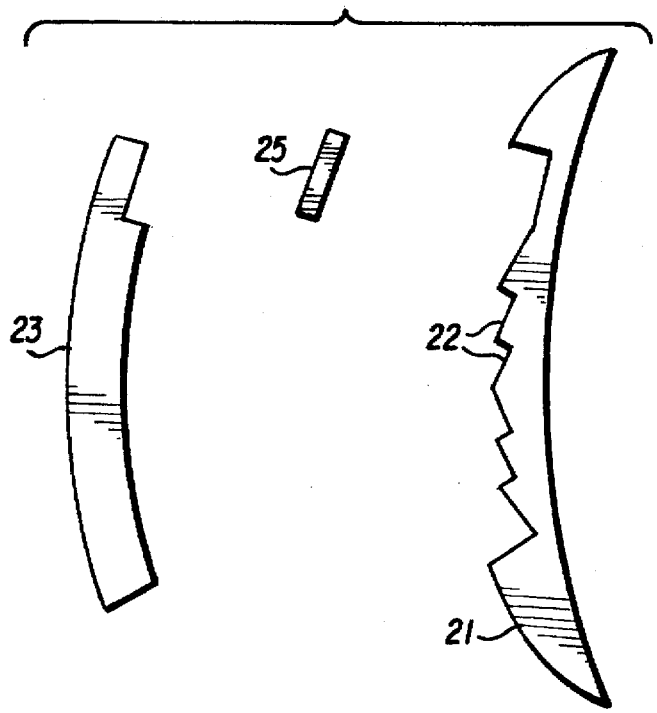
FIG. 4 is an exploded elevation of the second example of a lens assembly shown in FIG. 3.

A second form of device according to the present invention, which is of particular interest for applications requiring a thinner structure such as contact lenses, is to construct the lens itself as a switchable device. FIGS. 3 and 4 illustrate an example of this. The lens assembly 20 in this example includes a diffractive lens 21 formed of an isotropic material, perhaps by moulding, having annular steps 22 which provide the diffraction structure. A second isotropic component 23 forms a surface which matches the first except in the region of the diffractive structure formed by the annular steps 22. These two components 21, 23 together form a thin cell which contains a liquid crystal 24 in the spaces between the annular steps 22 and the second component 23. A photocell and electronics circuit 25 are provided in a further space between the isotropic components 21, 23 towards the periphery of the lens assembly 20.

In one example of the second form, the liquid crystal 24 is a nematic liquid crystal and is disposed so that, in its electrically unswitched state, either the ordinary or extraordinary refractive index of the liquid crystal is matched to that of the isotropic material of the components 21, 23. For one polarization, therefore, illumination passes through the structure without angular deviation by the diffractive lens structure and therefore passes to a focus defined solely by the refractive lens form. The angular deviation produced by the diffractive lens structure for the other, deviated, polarization varies across the aperture of the lens to produce a second distinct focus for this polarization. When the liquid crystal layer 24 is electrically switched by use of the photocell and electronics circuit 25, the refractive index of the liquid crystal becomes polarization-insensitive and the lens produces only a single focus.

A polarizer (not shown) may be provided in addition to the diffractive lens, so that the device can be arranged to switch from one monofocal state (for example 0D) to another monofocal state (say +3D), producing a true monovision switchable lens with two selectable foci. Where the liquid crystal cell does not contain a separate polarizer, in one state both foci are simultaneously produced and in that state the device behaves like a simultaneous vision lens, whilst in the other state (conveniently the distance-vision state), only one focus is produced.

According to a distinct, preferred embodiment of the invention, the lens assembly is an ophthalmic lens, preferably a contact lens, that is switchable between two states having different fixed focal lengths, independent of polarization, by the application of an electric field. For this embodiment, the contact lens transmits at least 90% of incident light, and preferably nearly 100% of incident light, at each of the two focal lengths. The two focal lengths will normally correspond to desired near and distance vision corrections for the user.

The lens assembly of FIGS. 3 and 4 may contain a cholesteric liquid crystal instead of a conventional nematic. Cholesterics are nematics which are doped with a compound which forces the nematic molecular axes to form a helical structure. Such a structure does not significantly discriminate between polarization states if the product of the twist pitch and the birefringence is small, typically less than one wavelength of light. When the cholesteric material is driven with an applied field, it switches to a second non-birefringent state of different refractive index in a similar way to conventional twisted nematic liquid crystals. Accordingly, a diffractive lens constructed in this way is a true monovision switchable lens (since a single, switchable focus is always provided), but is also independent of polarization. Since it requires no additional polarizers (that absorb typically half of the incident illumination), it always transmits practically 100% of incident light, thus providing greater visibility for the wearer in low lighting conditions.

The diffractive lens of FIGS. 3 and 4 is preferably designed such that there is a full wavelength phase mismatch at the boundary of the zones of the diffractive lens, such that the light is deviated with the minimum of diffraction into unwanted orders that otherwise, if allowed, would produce other foci. Calculations show that there is only 0.9% loss of light into unwanted diffraction orders in this condition.

The second example described above with reference to FIGS. 3 and 4, and each of its variants, has the advantage of a very thin cell structure (calculated to be minimum 3 microns thick with existing liquid crystal materials) so that very small quantities of liquid material are required (around 100 $pm^3$ for a contact lens). This reduces the likelihood of toxic side effects or other forms of bio-incompatibility in the event of leakage or diffusion and largely retaining the mechanical, chemical and gas permeability properties of the isotropic material, which may potentially be a conventional contact lens material.

The liquid crystal used in any of the examples described above may have ferroelectric properties. Ferroelectrics have the advantage of intrinsic bistability, so that a drive voltage is only required to switch the device; no electrical power is required at other times.

In any of the above examples of the device, the electrical control may be achieved by placing the power source 4 and control circuit 15 outside the optical area (in the iris area of a contact lens for example). Electrical contact may be made to the liquid crystal by use of electrode patterns similar to those used in a conventional liquid crystal cell.

Figure 5:
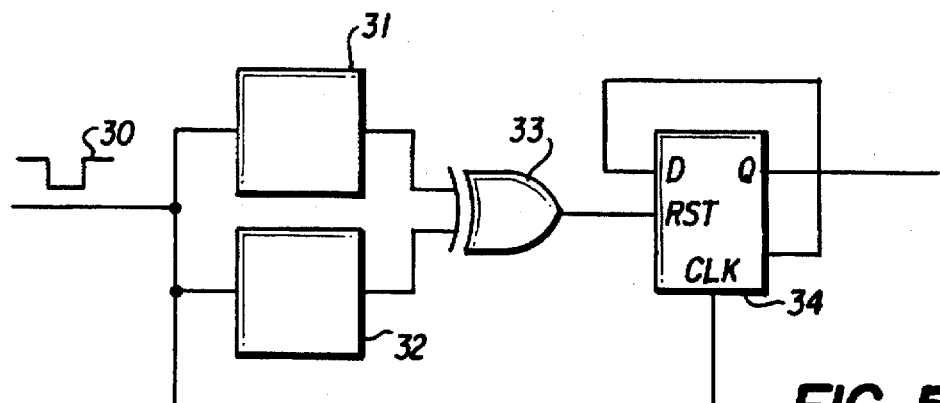
FIG. 5 is a circuit diagram of a switching circuit.

An example of a switching circuit is shown in FIG. 5. The output 30 from a photodiode is applied to the respective inputs of two monostables 31, 32 in parallel. The output pulse of one monostable 31 may have a duration of say 120 ms and the output pulse of the other monostable 32 may have a duration of say 80 ms. The outputs of the monostables 31, 32 are applied to respective inputs of an Exclusive-Or gate 33. The output of the Exclusive-Or gate 33 is passed to the reset input of a D-type flip-flop 34, the output Q of which provides a switching signal. The input signal 30 is also passed to the clock input of the flip-flop 34.

If the user blinks for a period of between 80 and 120 ms, the output 30 of the photodiode drops for that period. Each of the monostables 31, 32 is triggered. As the input pulse 30 is low between 80 and 120 ms, the Exclusive-Or gate 33 provides a HIGH output during that period to the flip-flop 34, thus toggling the Q output of the flip-flop 34 from HIGH to LOW or vice versa, providing an appropriate switching signal.

The bulk of the power requirement is for the drive electronics. With a low leakage integrated device similar in form to that used by an electronic calculator, the power requirement is around 30 microwatts. This is required during the cell switch time. For a ferroelectric liquid crystal, the switching time is around 10 microseconds. For example, if the user wishes to switch the device once every minute, the average power consumption will be 5 pW. This power must be generated by the photocell or battery. Consider use of a photocell: in a dimly lit room, the optical power available will be around 10% of the bulb rated power, around 10 W typically, distributed around a wall area of say 50 $m^2$, giving an illumination of 0.2 $W/m^2$, or 0.2 microwatts/$mm^2$. A 1 mm square silicon photodiode has a power conversion efficiency of about 30% in the visible wavelength range and therefore provides 60 nW, which is ample average power to switch a ferroelectric device.

A cholesteric device requires a drive voltage of 8 to 10V which preferably on average has little or no DC content (liquid crystals slowly hydrolyze when a DC field is applied to them). If it is assumed that the device has a capacitance of around 150 pF, the energy lost each time the potential is reversed, given by $½ CV^2$, is around 7.5 nJ. If the device is refreshed every ten seconds, the average power consumption of the cell is 75 nW, similar to the power produced by a 1 mm square silicon photodiode in dim room lighting.

A battery can also conveniently supply this level of power for long durations. A miniature battery can be constructed using two electrodes of dissimilar materials, preferably metals, whereby the system generates a current when both electrodes are in contact with a common electrolyte. The electrodes may take many forms. They may be printed onto a surface, fabricated from electrode material, or constructed by dispersing particles of the electrode material in an inert matrix such that conduction of electricity may occur across the matrix.

The battery may be produced in an inert state where no current is passed until the battery is immersed in liquid. Such fluid may be the tear film in contact with the eye. This feature may be provided by constructing a battery cell where the whole cell is enclosed, but where a membrane provides access to ions or water from the outside of the device. Water or ions diffusing into the device activates the battery. It may be desirable to utilize a membrane which does not allow ions from the electrodes to pass across the membrane to the outside of the device.

In one form, the battery consists of two planar electrodes separated by a small gap. In this gap there is held a partially dehydrated gel containing electrolyte. The whole cell is separated from the exterior by a water-permeable membrane. As a result of the partial dehydration, the gel does not fill the gap between the electrodes and no current can pass. When the contact lens comes in contact with the eye, water crosses the selective membrane causing the gel to swell to fill the void. The electrodes are then connected by electrolyte and current flows.

In a second form, the battery consists of two electrodes with a crystalline salt electrolyte held between them. Passage of water across a membrane activates the battery by hydration of the crystalline electrolyte.

Figure 6:
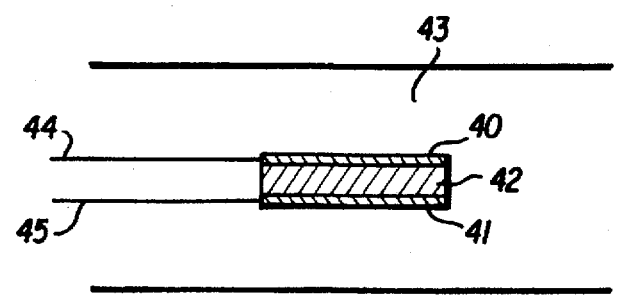
FIG. 6 is a diagram showing a battery.

In a third form, shown in FIG. 6 as an example, the battery consists of a copper electrodes 40 and a zinc electrode 41 separated by a dehydrated polymer electrolyte 42. A selective membrane 43 surrounds the electrodes 40, 41 and wires 44, 45 pass through the membrane 43 to the respective electrodes 40, 41. Hydration of the polymer electrolyte 42 by water passing through the membrane 43 activates the battery. The use of a polymer electrolyte 42 has the advantage that this material has high molecular weight and is therefore readily contained by a membrane. It is possible and desirable to select a membrane material that will allow the passage of water molecules, but that will reject the high molecular weight electrolyte and ions from the electrodes.

In a fourth form, the battery may consist of two electrodes alone. Immersing the system in tear fluid provides the electrolyte required to complete the circuit.

In a fifth form, the battery may consist of two electrodes in contact with a dehydrated gel. Immersion in tear fluid both hydrates the gel and provides the ions for the electrolyte. The gel helps to localize ions from the electrodes.

An organic chelating agent may be provided within those battery configurations having a membrane. This chelating agent may be employed to allow movement of ions within the cell while preventing them from migrating across the membrane.

Contact lenses according to the present invention can provide the advantage of allowing the user to select near or distance vision in a simple manner and can reduce or avoid the difficulties associated with simultaneous-vision bifocal lenses while retaining the advantages of bifocal lenses. Mechanical, chemical and gas permeability, and biocompatibility properties are determined by the encapsulating material which may be a conventional ophthalmic lens material.

I claim:

1. A lens assembly comprising:

a lens including a layer of cholesteric liquid crystal having a property which may be switched by application of an electric or magnetic field, said property being at least one of focal length, absorption, color and effective aperture, without employing a polarizer;

switching means coupled to the lens to provide a drive impulse to switch the property of the lens; and a power source coupled to the switching means to provide power for the switching means.

2. An assembly according to claim 1 wherein the lens is sealed and has no external connections.

3. An assembly according to claim 1 wherein the power source is a battery.

4. An assembly according to claim 1 wherein the power source is a photocell.

5. An assembly according to claim 1 which is an ophthalmic lens.

6. An assembly according to claim 1 which is a contact lens or an intraocular lens.

7. A lens assembly comprising:

a lens having a property which may be switched by application of an electric or magnetic field, said property being at least one of focal length, absorption, color and effective aperture;

switching means coupled to the lens to provide a drive impulse to switch the property of the lens;

a power source coupled to the switching means to provide power for the switching means; and wherein the switching means includes means for detecting a drop in a level of ambient light and changing the property of the lens when the level of detected light level drops for longer than a predetermined period of time.

8. An assembly according to claim 7 wherein the lens includes a birefringent lens and a layer of liquid crystal adjacent thereto.

9. An assembly according to claim 8 further comprising a polarizer.

10. An assembly according to claim 7 wherein the lens includes a diffractive lens and a layer of liquid crystal.

11. An assembly according to claim 10 further comprising a polarizer.

12. An assembly according to claim 10 wherein the liquid crystal is nematic.

13. An assembly according to claim 10 wherein the liquid crystal is ferroelectric.

14. An assembly according to claim 14 wherein the liquid crystal contains a dichroic dye.

15. An assembly according to claim 7 for use in proximity to at least one eye of a user wherein the switching means is activatable in response to a deliberate blinking of the eye of the user for an extended, predetermined period of time.

16. An assembly according to claim 7 wherein the switching means includes means for detecting a drop in the level of ambient light and changing the focal length of the lens when the detected light level drops for longer than a predetermined period of time.

17. A lens assembly comprising:

a lens having a property which may be switched by application of an electric or magnetic field, said property being at least one of focal length, absorption, color and effective aperture;

switching means coupled to the lens to provide a drive impulse to switch the property of the lens; and a power source coupled to the switching means to provide power for the switching means wherein the power source is a battery which is operable using tear fluid.

18. A lens assembly comprising:

a lens including a layer of liquid crystal which may be switched between two different focal lengths, independent of polarization of the incident light, by application of an electric or magnetic field;

switching means coupled to the lens to provide a drive impulse to switch the focal length of the lens; and a power source coupled to the switching means to provide power for the switching means.

19. An assembly according to claim 18 wherein the liquid crystal is cholesteric.

20. An assembly according to claim 18 wherein the lens transmits at least 90% of incident light at each of the two focal lengths.

21. An assembly according to claim 20 wherein the power source is a battery which is operable using tear fluid.

22. An assembly according to claim 20 for use in proximity to an eye of a user wherein the switching means is activatable by a deliberate blinking of the eye of the user for an extended predetermined period of time.

23. An assembly according to claim 18 wherein the lens transmits nearly 100% of incident light at each of the two focal lengths.

24. An assembly according to claim 18 wherein the assembly is a contact lens or an intraocular lens.

* * * * *